United States Patent [19]

Baba et al.

[11] Patent Number: 5,029,587
[45] Date of Patent: Jul. 9, 1991

[54] ULTRASONIC DIAGNOSTIC APPARATUS FOR OPHTHALMOLOGY

[75] Inventors: Yukio Baba, Hiroshima; Tadashi Kajino, Okazaki, both of Japan

[73] Assignee: Nidek Co., Ltd., Gamagori, Japan

[21] Appl. No.: 313,203

[22] Filed: Feb. 21, 1989

[30] Foreign Application Priority Data

Feb. 24, 1988 [JP] Japan ................................. 63-41434

[51] Int. Cl.[5] ............................................. A61B 8/00
[52] U.S. Cl. ............................ 128/660.07; 128/661.06
[58] Field of Search ...................... 128/660.01, 660.07, 128/661.06

[56] References Cited

U.S. PATENT DOCUMENTS

| | | | |
|---|---|---|---|
| 4,228,804 | 10/1980 | Holasek et al. | 128/660 |
| 4,564,018 | 1/1986 | Hutchison et al. | 128/660 |
| 4,662,380 | 5/1987 | Riley | 128/660.07 |
| 4,785,818 | 11/1988 | Hardin | 128/660.07 |
| 4,787,393 | 11/1988 | Fukukita et al. | 128/660.07 |

FOREIGN PATENT DOCUMENTS 0080483 2/1985 European Pat. Off. .
3150408 A1 7/1983 Fed. Rep. of Germany .

OTHER PUBLICATIONS

Trier, "Die Ultraschall-Chirugie und-Diagnostik in der Augenheilkinde", *Medizintachnik*, 104, Jg 6/84, pp. 216-221.
Ossoinig, K., "Echographic Detection and Classification of Posterior Hyphemas", *Ophthalmological*, vol. 189, pp. 2-11 (1984).

*Primary Examiner*—Francis Jaworski
*Attorney, Agent, or Firm*—Armstrong, Nikaido, Marmelstein, Kubovcik, & Murray

[57] ABSTRACT

A novel ultrasonic diagnostic apparatus for ophthalmology is disclosed in which a plurality of reflection echo images having a dynamic range larger than a display are stored, an image of a given condition is retrieved from the reflection echo images thus stored, and the image thus retrieved is displayed. As many diagnostic data as possible are obtained from a single frozen image thereby to produce acoustic information on a biological tissue.

8 Claims, 3 Drawing Sheets

ULTRASONIC DIAGNOSTIC APPARATUS FOR OPHTHALMOLOGY

FIELD OF THE INVENTION

The present invention relates to an ultrasonic diagnostic apparatus for ophthalmology in which an ultrasonic wave is transmitted from an ultrasonic transducer and an echo, reflected from the tissue at each part within an organism, is received so that the ultrasonic signal thus received is processed with waveforms or the like displayed. The present invention also relates to an ultrasonic diagnostic apparatus for ophthalmology suitable for precision diagnosis of a biological tissue with a fine structure such as the eye.

BACKGROUND OF THE INVENTION

The use of a diagnostic apparatus using and ultrasonic wave for obtaining information on the internal parts of organs of a person is rapidly advancing. The marked progress of the image processing technique has permitted the utilization of an economical ultrasonic wave with low invasiveness and other superior characteristics as compared with the existing ones for diagnosis.

The ultrasonic diagnostic apparatus is widely known in either 1) A mode type method in which a wave reflected from an object is displayed as a waveform (i.e., a single position) on a cathode ray tube or 2) B mode type method in which a single, obtained by an A mode method and subjected to intensity modulation, is used to scan a transducer thereby to display a section (i.e., a plurality of single positions from the A mode method) as an image.

The ultrasonic diagnosis for ophthalmology is generally divided into a basic examination, intended primarily for screening, and a special examination for analyzing the essential conditions of a morbid part or differential diagnosis. The special examination is further subdivided into i) a morphological differentiation for locating an affected part and determining the area covered except for more dynamic affected parts, and ii) a tissue differentiation for identifying the cause of the morbidity.

The B mode method is more widely used in the medical field. In ophthalmology, however, a method of tissue differentiation by a A-mode method is more established and developed than by a B-mode method and therefore both methods are used in combination taking advantage of the respective merits thereof.

The A-mode method permits determination of the acoustic characteristics of a focus by high or low response of a reflected wave as well as measurement between different tissues in the eye. In the tissue differentiation by the A-mode method of the conventional apparatuses, complete image processing is difficult, and therefore the minimum decibel value (dB) necessary for a spike from the morbid part to reach a mark line of a predetermined height is determined by changing the gain (also called the sensitivity) of an amplifier. Then the minimum decibel value of a spike from the sclera, which protects and holds the shape of the eyeball, is determined, so that the morbidity is estimated from the difference ($\Delta$ dB) between the two decibel values.

The B-mode diagnosis that has come to be widely used by ophthalmologists is useful for determining the range and size of a morbid part or anatomical morphological decision. The B-mode diagnosis of the conventional apparatuses requires a plurality of B-mode images for more three-dimensional tissue differentiation and employs a method in which each image, obtained by changing the sensitivity of the amplifier, is photographed by a Polaroid camera from Polaroid Corporation, U.S. or the like.

In view of the fact that the ultrasonic diagnostic apparatus for ophthalmologists is operated with an ultrasonic probe applied directly to the cornea of the patient under local anesthesia with the patient's lids retracted, a protracted diagnosis time imposes a heavy burden on the patient's. Further, the poor reproducibility of the apparatuses requires considerable skill on the part of the operator.

SUMMARY OF THE INVENTION

Accordingly, the object of the present invention is to provide an ultrasonic diagnostic apparatus in which, in view of the above-mentioned disadvantages of the conventional apparatuses, as much information as possible is obtained from a single A-mode waveform (image) and a B-mode image frozen and stored thereby to make an accurate diagnosis within a short time without imposing a heavy burden on the patient.

In order to achieve the aforementioned object, there is provided according to the present invention an ultrasonic diagnostic apparatus capable of producing acoustic data of the tissue of an organism by transmitting and receiving an ultrasonic wave. The apparatus comprises a device for storing a plurality of reflection echo images having a dynamic range larger than the display image, a device for retrieving an image of a given condition from the reflection echo images stored, and a device for displaying the same image.

The apparatus according to the invention further comprises a device for displaying, in characters and/or pattern, the width and area of the display of the image retrieved from the stored reflection echo images.

The apparatus according to the invention further comprises a device for displaying a plurality of images in divisions (sections).

DESCRIPTION OF THE PREFERRED EMBODIMENTS

An embodiment of the present invention will be explained below with reference to the accompanying drawings.

Figure 1:
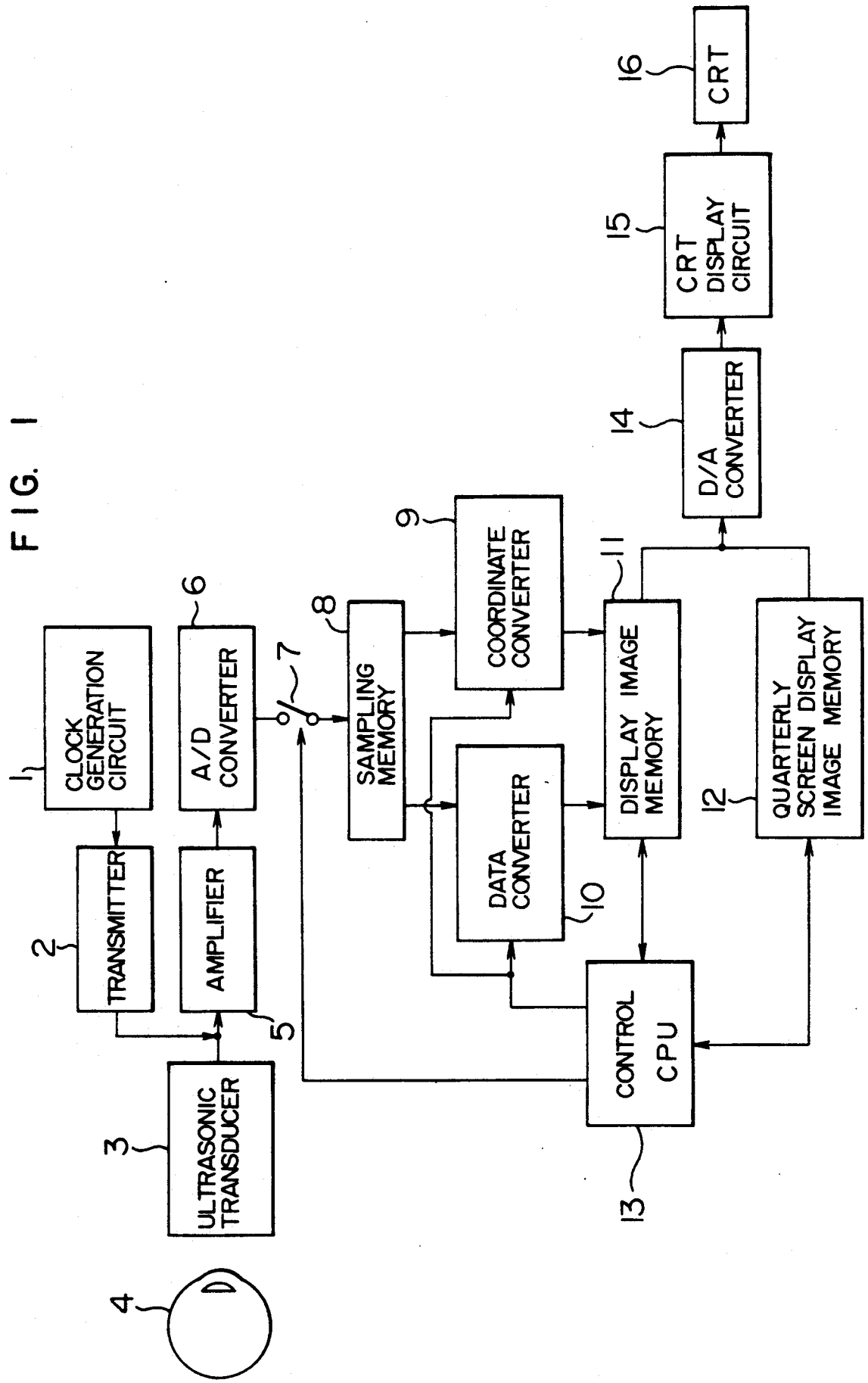
FIG. 1 is a block diagram showing a circuit according to an embodiment of the present invention.

FIG. 1 is a block diagram showing a first embodiment of the present invention.

Reference numeral 1 designates a clock generation circuit, numeral 2 a transmitter for converting the clock signal produced from the clock generation circuit 1 into a drive pulse for driving an ultrasonic transducer 3, and numeral 3 the ultrasonic transducer for transmitting an ultrasonic wave on the basis of a drive pulse from the transmitter 2 and receiving reflection echos from various parts of an eye 4 to be examined.

Numeral 5 designates an amplifier for amplifying the signal received from the ultrasonic transducer 3, numeral 6 an A/D converter for converting an amplified signal into a digital signal, and numeral 8 a sampling memory for storing the digital receiving signal as image data. The amplifier 5, the A/D converter 6 and the sampling memory 8 are set to a range wider than the dynamic range displayed on the CRT.

Numeral 7 designates a freezing switch.

Numeral 9 designates a coordinate converter for displaying a B-mode image on the CRT in the form of a sectored image, (i.e., converts data measured in a plurality of directions into a sector of a circle) numeral 10 a data converter for display in a given range, (i.e., selects the width of the range to be displayed within the original full-dynamic range) and numeral 11 a display image memory for storing the images displayed on the CRT.

According to this embodiment, a quarterly screen display image memory 12 is provided in addition to the display image memory 11. The quarterly screen display image memory 12 is not much different from the display image memory 11 and has the whole screen region thereof divided into four parts by software.

Numeral 13 designates a control CPU for controlling the operation of the above-mentioned component elements, i.e., controls the start/stop of converters 9, 10.

Numeral 14 designates a D/A converter for converting the digital data in the display image memories 11 and 12 into an analog data, numeral 15 a CRT display circuit, and numeral 16 a CRT.

Though not shown in the drawings, the width and area of the display range of the screen displayed on the CRT are indicated by characters and a band pattern.

The operation of the embodiment configured as above will be explained below.

Reference is made to the case in which display is possible of either an A-mode or a B-mode image in a given width range and an area of the display range.

First, the operator sets the object eye 4 and the ultrasonic transducer 3 in appropriate position in relationship to each other.

A clock signal generated from the clock generation circuit 1 is converted into a drive pulse in the transmitter 2, and supplied to the ultrasonic transducer 3. The ultrasonic wave generated by excitation of the ultrasonic transducer 3 is directed into the eyeball of the object eye 4.

The reflection echos from various parts of the interior of the eyeball are received by the ultrasonic transducer 3, and after being amplified by the amplifier 5, are supplied to the A/D converter 6, in which the intensity of each reflection echo is converted into a digital value and stored at a predetermined address point in the sampling memory 8 in the next stage.

The ultrasonic transducer 3 is sequentially scanned and signals for one screen are stored in the sampling memory 8.

At the time of freezing, the switch 7 is opened, and the A/D converter 6 is disconnected from the sampling memory 8, so that the immediately-preceding data is left in the sampling memory 8 thereby to fix the image data.

By operating an operating section (not shown), data of the required mode and dynamic range is designated from the image data fixed in the sampling memory 8. If the B-mode image is designated, for example, the image data stored in the sampling memory 8 is converted in coordinate by the coordinate converter 9 in response to a command from the control CPU 13 start/stop the coverison for the purpose of displaying the image as a sectored image.

In similar fashion, in changing the width or area of the display range, the data is converted to conform to the width and area of the display range by the data converter 10 based on a command from the control CPU 13 start/stop coverison.

Explanation will now be made about the process for changing the width and area of the display range after freezing.

Figure 2:
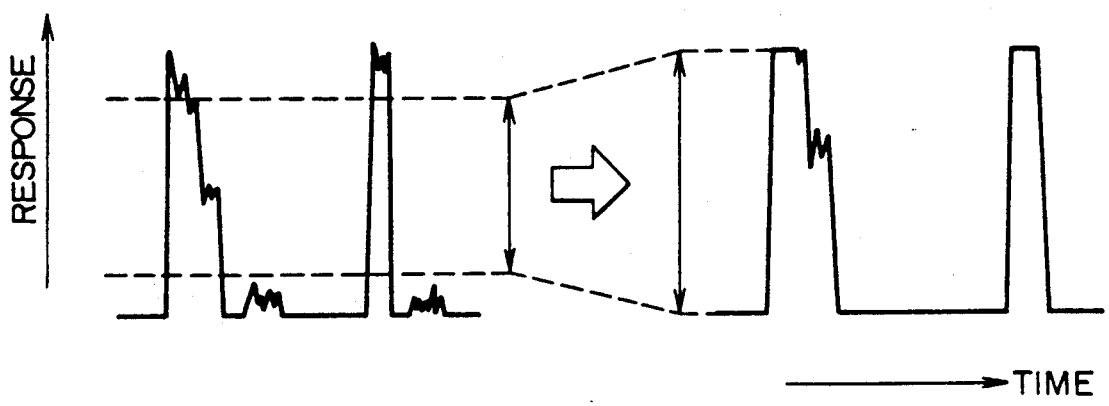
FIG. 2 is a graph showing the relationship between a reflection echo and a display waveform with a defined display range.

Normally, in A the or B mode, an input voltage in the sampled range is displayed on a display means having a predetermined display range after freezing. As a result, the reflection echos outside of the sampled range are not displayed. Specifically a lower region is cut and an upper region is saturated, so that it is impossible to diagnose whether such reflection echos are situated within the range on the display screen or how they are displaced (FIG. 2). In order to solve this problem, the apparatus comprises an amplifier, 5 an A/D converter 6 and a sampling memory 8 sufficiently meeting the signal requirement by having a dynamic range which is wider than the display range, and this area of the display range is shifted vertically while holding the range width. The regions not displayed thus come to appear, thereby assuring the same effect as if the gain of the amplifier is changed even after freezing.

Figure 3:
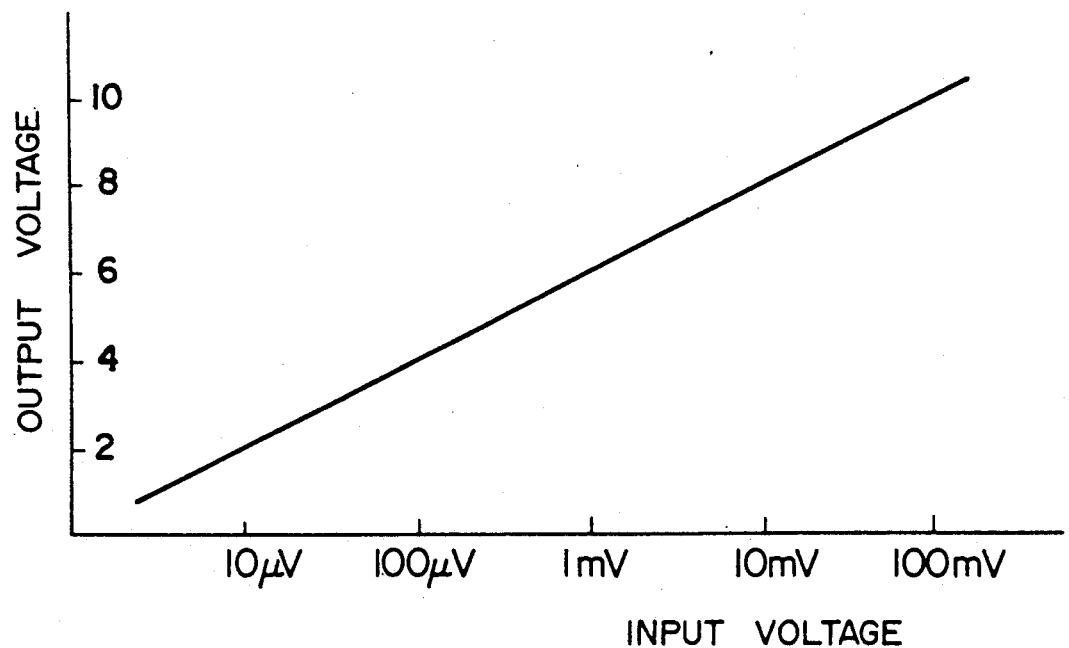
FIG. 3 is a graph showing the input-output characteristics of an amplifier.

Assume that the amplifier has a capacity of 80 dB sufficiently wider than the display dynamic range of 40 dB, for instance. The input-output characteristics of such an amplifier are shown in FIG. 3 which shows that the output voltage linearly changes with respect to logarithmic input voltage.

Figure 4:
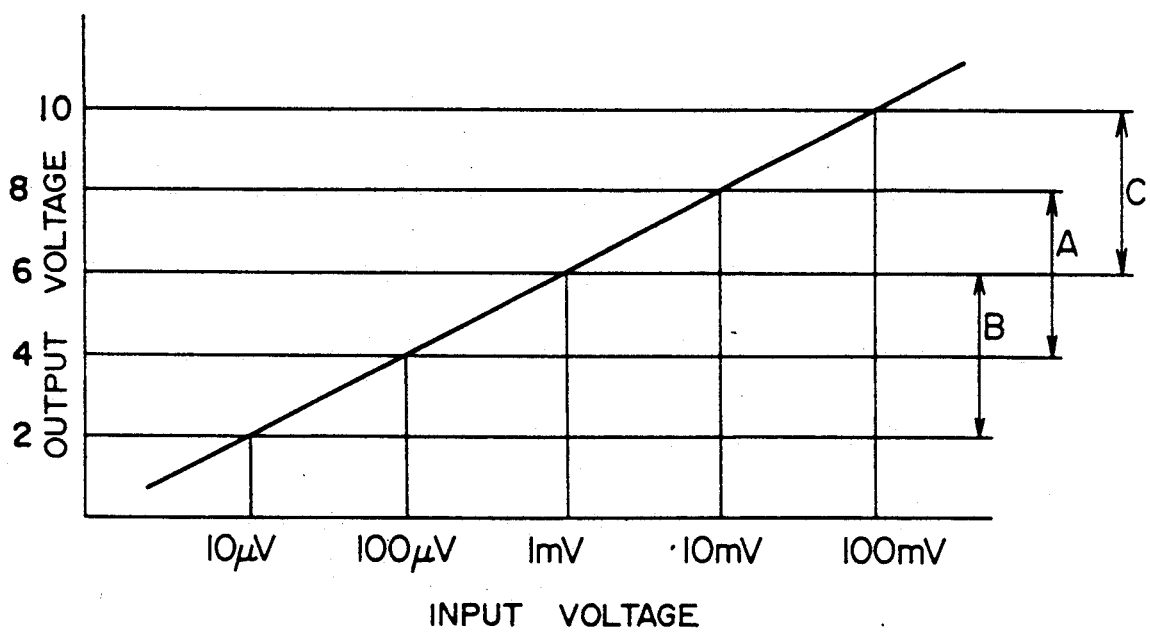
FIG. 4 is a graph showing the input-output characteristics with the display area selected while holding the width of the display range.

Now, assume that the apparatus displays the range width of 40 dB in the range area A in FIG. 4. When the apparatus is frozen, the reflection echo data is stored in all dynamic ranges of 80 dB as well as the portion A in the sampling memory 8. If the 40 dB width of the display area of A in FIG. 4 is held while selecting the range area of the portion B portion in FIG. 4, and the B which is one tenth of the input voltage of portion A in FIG. 4 is displayed as an output voltage equivalent to A, then it is possible to obtain the substantially the same effect as if the gain is increased by $$20 \, log 10 = 20 \, (dB)$$

In similar manner, the same effect as the reduction in the gain by 20 dB is obtained by selecting the range area of portion C in FIG. 4.

The data converted by these processes of operation are stored in the display image memory 11. A given B-mode image frozen is stored in a maximum of four screens together with the measurement and display conditions. Specifically, a B-mode image can be stored up to a maximum of four screens (images), and the stored images can be compared and observed on the same screen, thereby contributing to diagnostic conveniences.

Also, the quarterly screen display image memory 12 is capable of displaying a plurality of images of a single affected part of the patient in different directions of measurement at the same time and therefore can be used for providing more information to the operator.

In this way, the data stored in the display image memory 11 and the quarterly screen display image memory 12 are converted into analog signals by the D/A converter 14 and displayed on the CRT 16 through the CRT display circuit 15.

It will thus be understood from the foregoing description that according to the present invention a multiplicity of pieces of information are obtained from a single image frozen (stored), and therefore the burden on the patient is minimized.

Further, the fact that the required information can be obtained instantaneously facilitates the diagnosis while at the same time making possible easy verification with high reproducibility.

We claim:

1. An ultrasonic diagnostic apparatus for ophthalmology comprising:
    an ultrasonic means for transmitting and receiving ultrasonic waves and for outputting a plurality of ultrasonic reflection echo images therefrom;
    storage means for storing said plurality of ultrasonic reflection echo images having a larger dynamic range than a display image range;
    retrieval means for retrieving an image from the ultrasonic reflection echo images stored in said means storage and for selecting a desired strong or weak echo area of said larger dynamic range while maintaining a same width of the display image range; and
    display means responsive to said retrieval means for displaying said selected echo areas of said image retrieved as a display image, wherein acoustic data for diagnosis on an area of interest based on an ultrasonic wave transmitted and received as said ultrasonic reflected echo image is produced.

2. An ultrasonic diagnostic apparatus for ophthalmology according to claim 1, wherein said retrieval means includes means for selecting said width of said display image range.

3. An ultrasonic diagnostic apparatus for ophthalmology according to claim 1, further comprising means for displaying the dynamic range of the image retrieved from the stored reflection echo images in characters and/or a pattern.

4. An ultrasonic diagnostic apparatus for ophthalmology according to claim 1, wherein said display means includes plural-screen divided display means.

5. An ultrasonic diagnostic apparatus for ophthalmology according to claim 4, wherein said plural-screen divided display means is a quarterly screen display image memory.

6. An ultrasonic diagnostic apparatus for ophthalmology according to claim 1, wherein said storage means is a sampling memory for storing received ultrasonic signals digitized as image data.

7. An ultrasonic diagnostic apparatus for ophthalmology according to claim 1, wherein said retrieval means includes a data converter, a coordinate converter and a control CPU for controlling said converters.

8. An ultrasonic diagnostic apparatus for ophthalmology according to claim 1, wherein said display means is a cathode ray tube.

* * * * *